United States Patent [19]

Yahner

[11] 3,979,453

[45] Sept. 7, 1976

[54] 3-CYANAMINO-2,6-DINITROANILINES

[75] Inventor: Joseph A. Yahner, New Palestine, Ind.

[73] Assignee: Eli Lilly and Company, Indianapolis, Ind.

[22] Filed: June 23, 1975

[21] Appl. No.: 589,313

[52] U.S. Cl. ............... 260/551 C; 71/118; 260/295 AM; 260/501.1; 260/577; 424/320
[51] Int. Cl.² .................................. C07C 125/08
[58] Field of Search ............... 260/551 C, 295 AM; 71/105, 121; 424/304, 320

[56] References Cited
UNITED STATES PATENTS

| | | | |
|---|---|---|---|
| 2,212,825 | 8/1940 | Daudt et al. | 260/571 |
| 3,111,403 | 11/1963 | Soper | 71/2.3 |
| 3,257,190 | 6/1966 | Soper | 71/2.3 |
| 3,321,292 | 5/1967 | Soloway | 71/2.3 |
| 3,332,769 | 7/1967 | Soper | 71/121 |
| 3,367,949 | 2/1968 | Soper | 260/397.7 |
| 3,617,251 | 11/1971 | Hunter et al. | 71/121 |
| 3,617,252 | 11/1971 | Hunter et al. | 71/121 |
| 3,672,864 | 6/1972 | Maravetz | 71/103 |
| 3,672,866 | 6/1972 | Damiano | 71/121 |
| 3,764,624 | 10/1973 | Strong et al. | 260/574 |
| 3,781,323 | 12/1973 | Wagner et al. | 71/105 X |
| 3,849,107 | 11/1974 | Fischer | 71/121 X |
| 3,877,924 | 4/1975 | Fischer | 71/121 X |
| 3,888,897 | 6/1975 | Martin | 260/556 B X |
| 3,910,783 | 10/1975 | Hunter et al. | 71/105 |

FOREIGN PATENTS OR APPLICATIONS 816,837   6/1974   Belgium

OTHER PUBLICATIONS

Joshi et al., CA 28:469 (1934).
Borsche et al., CA 5:2079 (1911).
Deutsche Chem. Gesell. Ber., 43, Hantzsch, pp. 1662–1685, (1910).

*Primary Examiner*—Robert V. Hines
*Assistant Examiner*—Thomas A. Waltz
*Attorney, Agent, or Firm*—Leroy Whitaker; Everet F. Smith

[57] ABSTRACT

A new class of 3-cyanamino-2,6-dinitroanilines has been discovered. The novel cyanamino compounds of this invention exhibit fungicidal activity against *Plasmopara viticola*, the causative organism of grape downy mildew.

6 Claims, No Drawings

3-CYANAMINO-2,6-DINITROANILINES

BACKGROUND OF THE INVENTION

1. Field of the Invention

This invention relates to a new class of 2,6-dinitroanilines. More particularly, this invention relates to 3-cyanamino-2,6-dinitroanilines.

2. Description of the Prior Art

Various 2,6-dinitroanilines have been disclosed in the prior art. Borsche et al., C.A. 5, 2079 (1911); Hantzsch, Deutsche Chemische Gesellschaft Berichte, 43, 1662–1685 (1910); Joshi et al., C.A. 28, 469 (1934); and Daudt et al., U.S. Pat. No. 2,212,825 describe various 2,6-dinitroanilines. In the early 1960's, Soper disclosed that many 2,6-dinitroanilines possess herbicidal activity and he added many new compounds to the art. See, for example, U.S. Pat. Nos. 3,111,403; 3,257,190; 3,332,769; and 3,367,949. Following Soper's lead, a large number of related dinitroanilines have also been shown to possess similar herbicidal activity. See, for example, U.S. Pat. Nos. 3,321,292; 3,617,251; 3,617,252; 3,672,864; 3,672,866; 3,764,624; and 3,877,924; and Belgian Pat. No. 787,939.

SUMMARY OF THE INVENTION

I have now discovered a new class of 3-cyanoamino-2,6-dinitroanilines having the formula:

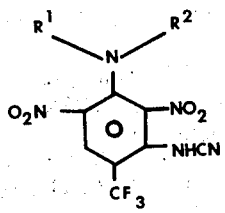

wherein
R[1] is hydrogen, $C_1$–$C_4$ nontertiary alkyl, $C_3$–$C_4$ alkenyl, chloro $C_2$–$C_3$ alkyl, chloro $C_3$–$C_4$ alkenyl or cyclopropylmethyl; and
R[2] is $C_1$–$C_7$ nontertiary alkyl, $C_3$–$C_4$ alkenyl, chloro $C_2$–$C_3$ alkyl, chloro $C_3$–$C_4$ alkenyl or cyclopropylmethyl;
and the triethylamine, pyridine and alkali metal salts thereof.

My novel compounds exhibit herbicidal and fungicidal activity. The compounds are particularly active against *Plasmopara viticola*, the causative organism of grape downy mildew.

DESCRIPTION OF THE PREFERRED EMBODIMENT

As used in this specification, all the terms appearing in the above description of my compounds have their usual meanings Exemplary of the compounds coming within the scope of my invention are the following:
  N-(2-butyl)-3-cyanamino-2,6-dinitro-4-trifluoromethylaniline
  3-cyanamino-N,N-diethyl-2,6-dinitro-4-trifluoromethylaniline
  3-cyanamino-2,6-dinitro-N-(4-heptyl)-4-trifluoromethylaniline
  3-cyanamino-2,6-dinitro-N-ethyl-N-n-propyl-4-trifluoromethylaniline
  N-(2-chloroethyl)-3-cyanamino-2,6-dinitro-N-n-propyl-4-trifluoromethylaniline
  N-allyl-3-cyanamino-2,6-dinitro-N-ethyl-4-trifluoromethylaniline
  3-cyanamino-2,6-dinitro-N-ethyl-N-methallyl-4-trifluoromethylaniline
  N-n-butyl-3-cyanamino-2,6-dinitro-N-ethyl-4-trifluoromethylaniline
  N-(2-chloroallyl)-3-cyanamino-2,6-dinitro-N-n-propyl-4-trifluoromethylaniline
  3-cyanamino-N-cyclopropylmethyl-2,6-dinitro-N-n-propyl-4-trifluoromethylaniline The cyanamino compounds of my invention are sufficiently acidic to form salts with strong bases, such as tertiary amines and alkali metal hydroxides. Therefore, my invention includes within its scope salts of my compounds, such as the triethylamine, pyridine, and alkali metal salts.

My 3-cyanamino-2,6-dinitroanilines are prepared by reaction of the corresponding 3-chloro compound with cyanamid in the presence of a strong base. The corresponding 3-chloro-2,6-dinitroaniline is, in turn, prepared by the reaction of the appropriate amine with 2,4-dichloro-3,5-dinitrobenzotrifluoride as described in U.S. Pat. No. 3,617,252.

The reaction of cyanamid with a 3-chloro-2,6-dinitroaniline is preferably conducted in an inert solvent at a temperature within the range from about 25°C. to 100°C. Suitable inert solvents include ethanol, dioxane, tetrahydrofuran, and the like. The reaction is conveniently conducted at the reflux temperature of such solvent. Reaction times vary from a few hours to a few days, such as from about six hours to about six days. Upon completion of the reaction, the reaction mixture is allowed to cool and poured over ice to precipitate the product.

The preparation of my novel cyanamines will be illustrated by the following example.

EXAMPLE 1

A mixture of 40 gm. of 3-chloro-2,6-dinitro-N-(3-pentyl)-4-trifluoromethylaniline, 10.5 gm. of cyanamid, and 30 gm. of triethylamine in 250 ml. of 3A ethanol was heated under reflux for five days. The solution was allowed to cool and was poured over ice-water. The product which precipitated was removed by filtration and recrystallized from 3A ethanol and water to give 36 gm. (71%) of the triethylamine salt of 3-cyanamino-2,6-dinitro-N-(3-pentyl)-4-trifluoromethylaniline, m.p. 135°–137°C. The structure was confirmed by the NMR and IR spectra and elemental analysis.

Calculated: C, 49.35; H, 6.32; N, 18.17
Found: C, 49.56; H, 6.06; N, 18.37

Following the procedure of Example 1, the following additional representative compounds of my invention were prepared. All the compounds were isolated as the triethylamine salt.
  3-cyanamino-2,6-dinitro-N,N-di-n-propyl-4-trifluoromethylaniline, triethylamine salt, m.p. 102°–103°C.
  3-cyanamino-N,N-diethyl-2,6-dinitro-4-trifluoromethylaniline, triethylamine salt, m.p. 122°–124°C.
  3-cyanamino-2,6-dinitro-N-n-propyl-4-trifluoromethylaniline, triethylamine salt, m.p. 130°–131°C.

3-cyanamino-2,6-dinitro-N-ethyl-N-methyl-4-trifluoromethylaniline, triethylamine salt, m.p. 84°–86°C.

My novel 3-cyanamino-2,6-dinitroanilines are useful in the control of *Plasmopara viticola*, the causative organism of grape downy mildew. They also exhibit some herbicidal activity. When used as fungicides, they are employed in accordance with techniques known in the agricultural art.

My novel compounds are preferably employed in liquid, powder, or dust compositions containing one or more of the active compounds. In preparing such compositions, the cyanamino compounds can be modified with one or more of a plurality of additaments including organic solvents, petroleum distillates, water or other liquid carriers, surface active dispersing agents, and finely divided inert solids. In such compositions, the cyanamino compound can be present in a concentration from about 2 to 98% by weight.

In the preparation of dust compositions, my compounds can be formulated with any of the finely divided solids, such as pyrophyllite, talc, chalk, gypsum, and the like. In such operations, the finely divided carrier is ground or mixed with the cyanamino compound or is wet with a solution of the compound in a volatile organic solvent. Similarly, dust compositions containing the active compound can be prepared with various solid surface active dispersing agents, such as fuller's earth, bentonite, attapulgite, and other clays. Depending upon the proportions of ingredients, these dust compositions may be employed as such or may be diluted with an additional solid surface active dispersing agent or with pyrohyllite, chalk, talc, gypsum, and the like, to obtain the desired amount of active ingredient in the final composition. Also, such dust compositions can be dispersed in water with or without the aid of dispersing agents to form liquid sprayable mixtures.

The cyanamino compounds or a liquid or dust concentrate composition containing one or more of such compounds can be incorporated in intimate mixture with surface active dispersing agents, such as nonionic emulsifying agents, to form spray compositions. Such compositions may be employed as such or may be dispersed in liquid carriers to form diluted sprays containing the active compound in any desired amount.

Similarly, the active compounds can be formulated with a suitable water-immiscible organic liquid and a surface active dispersing agent to produce emulsifiable concentrates which can be further diluted with water and/or oil to form spray mixtures in the form of oil-water emulsions. Preferred dispersing agents to be employed in these compositions are oil-soluble and include the nonionic emulsifiers, such as condensation products of alkylene oxides with phenols, sorbitan esters, complex ether alcohols, and the like. Suitable organic liquids which can be employed include petroleum oils and distillates, toluene, and the synthetic organic oils. The surface active dispersing agents are usually employed in liquid compositions in the amount of from 0.1 to 20% by weight of the composition.

The amount of the cyanamino compound for use in the control of grape downy mildew can vary widely, provided that an effective amount is used. The amount which is effective is dependent upon the particular compound employed and the severity of the downy mildew infection. In general, when used in the control of downy mildew, the compounds are employed at a rate of from about 10 gm. to 2 kg. per hectare. For such use, the compounds are applied to the foliage of the host plant.

I claim:
1. A compound of the formula:

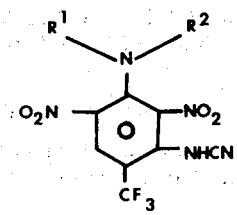

wherein
R¹ is hydrogen $C_1$–$C_4$ nontertiary alkyl, $C_3$–$C_4$ alkenyl, chloro $C_2$–$C_3$ alkyl, chloro $C_3$–$C_4$ alkenyl or cyclopropylmethyl; and
R² is $C_1$–$C_7$ nontertiary alkyl, $C_3$–$C_4$ alkenyl, chloro $C_2$–$C_3$ alkyl, chloro $C_3$–$C_4$ alkenyl or cyclopropylmethyl;
and the triethylamine, pyridine and alkali metal salts thereof.

2. The compound of claim 1 which is 3-cyanamino-2,6-dinitro-N-(3-pentyl)-4-trifluoromethylaniline.
3. The compound of claim 1 which is 3-cyanamino-2,6-dinitro-N,N-di-n-propyl-4-trifluoromethylaniline.
4. The compound of claim 1 which is 3-cyanamino-N,N-diethyl-2,6-dinitro-4-trifluoromethylaniline.
5. The compound of claim 1 which is 3-cyanamino-2,6-dinitro-N-n-propyl-4-trifluoromethylaniline.
6. The compound of claim 1 which is 3-cyanamino-2,6-dinitro-N-ethyl-N-methyl-4-trifluoromethylaniline.

* * * * *